US008075742B2

(12) United States Patent
Tarancon, III

(10) Patent No.: US 8,075,742 B2
(45) Date of Patent: Dec. 13, 2011

(54) APPARATUS AND PROCESS FOR THE SEPARATION AND PURIFICATION OF IDEAL AND NON-IDEAL REFRIGERANT MIXTURES

(75) Inventor: Gregorio Tarancon, III, Fort Myers, FL (US)

(73) Assignee: Midwest Refrigerants, LLC, Hollywood, FL (US)

( * ) Notice: Subject to any disclaimer, the term of this patent is extended or adjusted under 35 U.S.C. 154(b) by 0 days.

(21) Appl. No.: 12/630,684

(22) Filed: Dec. 3, 2009

(65) Prior Publication Data
US 2010/0218552 A1  Sep. 2, 2010

Related U.S. Application Data

(60) Provisional application No. 61/156,143, filed on Feb. 27, 2009.

(51) Int. Cl.
*B01D 3/14* (2006.01)
*B01D 3/36* (2006.01)
*C07C 17/383* (2006.01)
*F25J 3/02* (2006.01)

(52) U.S. Cl. ........... 203/67; 62/630; 62/631; 203/75; 203/78; 203/82; 203/84; 203/87; 570/178

(58) Field of Classification Search .............. 62/529, 62/630, 631; 203/2, 67, 75, 78, 82, 84, 87; 510/408; 570/178
See application file for complete search history.

(56) References Cited

U.S. PATENT DOCUMENTS

| | | | | |
|---|---|---|---|---|
| 3,930,536 A * | 1/1976 | Cherry et al. | .............. | 165/143 |
| 4,906,796 A | 3/1990 | Yates | | |
| 5,087,778 A | 2/1992 | Yates | | |
| 5,160,499 A | 11/1992 | Edwards | | |
| 5,250,156 A * | 10/1993 | Pucci et al. | .............. | 203/39 |
| 5,260,496 A | 11/1993 | Meinert et al. | | |
| 5,288,930 A | 2/1994 | Shields et al. | | |
| 5,467,601 A * | 11/1995 | Paolino et al. | .............. | 62/646 |
| 5,497,627 A | 3/1996 | Heyduk et al. | | |
| 5,585,529 A | 12/1996 | Corbin et al. | | |
| 5,830,325 A | 11/1998 | Mahler et al. | | |
| 5,919,340 A * | 7/1999 | Kohno et al. | .............. | 203/57 |
| 6,047,560 A | 4/2000 | Nishimura et al. | | |
| 6,797,125 B2 * | 9/2004 | Honkanen et al. | .............. | 203/71 |
| 6,848,501 B2 * | 2/2005 | Hirao et al. | .............. | 165/119 |
| 7,479,477 B2 * | 1/2009 | Wilson et al. | .............. | 510/408 |
| 7,553,397 B1 * | 6/2009 | Colley et al. | .............. | 203/14 |

FOREIGN PATENT DOCUMENTS

| | | |
|---|---|---|
| EP | 0503771 A1 | 9/1992 |
| WO | 9419301 A1 | 9/1994 |
| WO | 9924358 A1 | 5/1999 |

OTHER PUBLICATIONS

International Search Report for PCT/US2010/023334 dated Jun. 4, 2010.

* cited by examiner

*Primary Examiner* — Virginia Manoharan
(74) *Attorney, Agent, or Firm* — McKenna Long & Aldridge LLP

(57) ABSTRACT

An apparatus and process for the separation of refrigerant mixtures is provided. The apparatus includes a first distillation column, a first condenser, and a first collection vessel. The apparatus also includes a sorter vessel that includes a sorter agent, wherein the sorter vessel is fluidly connected to the first distillation column.

12 Claims, 6 Drawing Sheets

APPARATUS AND PROCESS FOR THE SEPARATION AND PURIFICATION OF IDEAL AND NON-IDEAL REFRIGERANT MIXTURES

RELATED APPLICATIONS

This application claims priority to U.S. Provisional Patent Application Ser. No. 61/156,143, filed on Feb. 27, 2009, which is incorporated by reference in its entirety.

FIELD OF THE INVENTION

The present invention relates to ideal and non-ideal refrigerant mixtures and more specifically to a method and apparatus for separating and purifying refrigerant mixtures, including both ideal and non-ideal refrigerant mixtures.

BACKGROUND OF THE INVENTION

Following the end of the Second World War, chlorofluorocarbons (organic compounds that include carbon, chlorine and fluorine, hereinafter "CFCs", as well as those chlorofluorocarbon compounds having at least one hydrogen present, hereinafter "HCFCs") came into popular use as refrigerators replaced the traditional ice boxes. Refrigerants are capable of removing heat by cooling a space below the ambient temperature, and are typically used in a heat cycle, wherein the refrigerant undergoes a reversible phase change from a gas to a liquid, during which time heat is removed from a space. Thus, in addition to use in refrigerators, refrigerants also find uses in residential and business air conditioners, as well as in automobile air conditioning systems. Refrigerants have other uses as well, including use as foam blowing agents and in the pharmaceutical industry for asthma inhalers Studies, however, have linked CFCs to atmospheric ozone depletion. As a result, the Montreal Protocol (initially entered into force in 1989, and subsequently revised multiple times) mandated that CFCs no longer be used as refrigerants and their use was phased out during the period of 1987 to 1997. The use of chlorofluorocarbons as refrigerants has gradually been replaced by the use of fluorocarbons, including perfluorocarbons (FCs), hydrofluorocarbons (HFCs), and hydrochlorofluorocarbons (HCFCs). While manufacturing of chlorofluorocarbons (CFCs) has essentially ceased in view of the Montreal Protocol, existing supplies continue to have limited commercial value, for instance as inhalers in the health field. Because CFCs, HCFCs, FCs and HFCs are often present as azeotropic mixtures, each of the components of the mixture may have value, particularly if CFCs can be effectively separated from the other components. This would allow for compounds to be recycled, or for compounds to be more effectively destroyed or converted for disposal.

The fluorocarbon refrigerants currently in use (i.e., HCFCs, FCs and HFCs) exhibit chemical stability, non-flammability, chemical inertness, are safe to health, and do not deplete ozone from the atmosphere. The refrigerants have physical characteristics such as low melting points and boiling points appropriate for refrigerant use, low vapor heat capacity, low viscosity, high thermal conductivity, and good oil solubility.

Chlorofluorocarbons and fluorocarbons are conventionally referred to by a numbering convention wherein the rightmost digit denotes the number of fluorine atoms; the "tens" digit denotes one more than the number of hydrogen atoms; the "hundreds" digit (if present) denotes the number of carbon atoms less one (thus there may be no digit for this when the compound is a methyl halide). Further, although most of the refrigerant compounds are alkanes, if the compound contains any links of unsaturation, the number of double bonds can be indicated in numbering conversion as the "thousands" digit. There may also be a suffix, "a", "b", "c", to indicate isomers. Thus, HFC-134a has 4 fluorine atoms, 2 hydrogen atoms and 2 carbon atoms. The "a" suffix indicate that the F atoms are not equally distributed, but rather the compound is 1,1,1,2-tetrafluoroethane. In contrast, in referring to HFC-134, the fluorine atoms are equally distributed throughout the molecule and the compound is 1,1,2,2-tetrafluoroethane. The alkane based compounds are generally referred to as CFCs, HCFCs, FCs, and HFCs.

Because chlorofluorocarbons often form azeotropic mixtures with fluorocarbons, effective and efficient separation is frequently difficult. Therefore, in view of the current restrictions associated with chlorofluorocarbons, it has become both necessary and desirable to develop new methods to effectively and efficiently separate and purify the individual components from an azeotropic mixture. Various techniques have been developed to facilitate the separation of azeotropic mixtures, including the use of various zeolites and molecular sieves, for instance, as is described in U.S. Pat. Nos. 4,906,796; 5,087,778; 5,160,499; 5,260,496; 5,288,930; and 5,585,529. Each of the prior art techniques, however, have not been entirely satisfactory because the components of these azeotropic mixtures frequently have similar boiling points, thereby making it difficult to obtain highly pure components upon separation. In addition, the prior art zeolite/molecular sieve processes frequently require that the zeolite material or molecular sieves be changed and/or regenerated, thus requiring that the separation process be stopped for a period of time. In an exemplary prior art procedure employing zeolites and/or molecular sieves, as described in U.S. Pat. No. 5,497,627, a single stage azeotropic separation of a contaminated chlorofluorocarbon (i.e., CFC-12 contaminated with HCFC-22 and CFC-115) is processed using water as a solvent. It appears very little refrigerant is extracted and water remains with both extractants.

The process and apparatus described herein provide an apparatus that effectively and efficiently separates components for ideal mixtures (i.e., simple binary mixtures) and azeotropic mixtures (e.g., mixtures that include one or more CFC compound, in addition to at least one compounds from the group of HCFCs, HFCs, and FCs).

SUMMARY

The invention provides an improved method and apparatus for the separation of refrigerant fluid mixtures and the purification of the separated refrigerant fluids.

In one aspect, an apparatus for separating and purifying a refrigerant mixture is provided. The apparatus includes a fractionation component that includes a first distillation column, a first condenser, a first reboiler, and a first collection vessel for receiving separated and purified components. The first distillation column, the first condenser, the first reboiler, and the first collection vessel are fluidly connected. The apparatus also includes a sorter vessel that includes a sorter agent, wherein said sorter vessel is fluidly connected to the first storage vessel and the first distillation column.

In certain embodiments, the apparatus for separating and purifying the refrigerant mixture can further include a second fractionation component that includes a second distillation column, a second condenser, a second reboiler, and a second collection vessel for receiving separated and purified components. The second distillation column, the second condenser, the second reboiler, and the second collection vessel are fluidly connected. The apparatus further includes a heat exchanger, wherein the heat exchanger is fluidly connected to the first and second distillation columns, such that the heat exchanger is positioned to receive condensate from first and second condensers and to transfer the condensate from the first condenser to the second distillation column, and to transfer the condensate from the second condenser to the first distillation column.

In another aspect, a process for separating a refrigerant mixture comprising a first and second refrigerant component is provided. The process includes the use of an apparatus that includes a fractionation component that includes a first distillation column, a first condenser, a first reboiler, and a first collection vessel for receiving separated and purified components. The first distillation column, the first condenser, the first reboiler, and the first collection vessel are fluidly connected. The apparatus also includes a sorter vessel that includes a sorter agent, wherein said sorter vessel is fluidly connected to the first distillation column. The process includes the steps of: (1) introducing the refrigerant mixture into the sorter and contacting the refrigerant mixture with the sorter agent, wherein the step of contacting the refrigerant mixture with the sorter agent preferentially absorbs the first refrigerant component from the refrigerant mixture; (2) heating the sorter to a first pre-selected temperature to produce a second refrigerant vapor; (3) cooling the second refrigerant vapor and producing a second refrigerant component condensate, the second refrigerant component condensate being essentially free of the first refrigerant component; (4) collecting a second product stream, wherein the second product stream includes the second refrigerant component; (5) heating the sorter to a second pre-selected temperature to produce a first refrigerant vapor; (6) cooling the first refrigerant vapor and producing a first refrigerant component condensate, the first refrigerant component condensate being essentially free of the second refrigerant component; and (7) collecting a first product stream, wherein the first product stream includes the first refrigerant component.

In another aspect, a process for separating a refrigerant mixture comprising two refrigerant components is provided. The process includes the use of an apparatus that includes a fractionation component that includes a first distillation column, a first condenser, a first reboiler, a first collection vessel for receiving separated and purified components, a second fractionation component that includes a second distillation column, a second condenser, a second reboiler, and a second collection vessel for receiving separated and purified components. The first distillation column, the first condenser, the first reboiler, and the first collection vessel are fluidly connected. The second distillation column, the second condenser, the second reboiler, and the second collection vessel are fluidly connected. The apparatus further includes a heat exchanger, wherein the heat exchanger is fluidly connected to the first and second distillation columns, such that the heat exchanger is positioned to receive condensate from first and second condensers and to transfer the condensate from the first condenser to the second distillation column, and to transfer the condensate from the second condenser to the first distillation column. The apparatus also includes first and second sorter vessels that includes a sorter agent, wherein said sorter vessel is fluidly connected to the first distillation column. The process steps include the steps of: (1) introducing equal volumes of the refrigerant mixture into the first and second reboilers of the apparatus; (2) heating the refrigerant mixture in the first reboiler to a first pre-selected temperature such that a first reboiler produces a first refrigerant vapor; (3) heating the refrigerant mixture in the second reboiler to a second pre-selected temperature such that the second reboiler produces a second refrigerant vapor; (4) cooling the first refrigerant vapor in the first condenser to form a first refrigerant condensate; (5) cooling the second refrigerant vapor in the second condenser to form a second refrigerant condensate; (6) collecting a portion of the first refrigerant condensate from the first condenser and transferring it to the second fractionating column, wherein the first refrigerant condensate has a greater concentration of one component of the refrigerant mixture than the first refrigerant vapor; (7) collecting a portion of the second refrigerant condensate from the second condenser and transferring it to the first fractionating column, wherein the second refrigerant condensate has a greater concentration of one component of the refrigerant mixture than the second refrigerant vapor; (8) repeating the separation steps until the first and second refrigerant condensates reach a pre-selected purity; and then (9) collecting a first product stream that includes a portion of the first refrigerant condensate in a first collection vessel; and collecting a second product stream that includes a portion of the second refrigerant condensate in a second collection vessel.

In certain embodiments, the first pre-selected temperature is selected such that the temperature of the first refrigerant vapor in the first condenser is at a temperature that is greater than at least the boiling point of the refrigerant mixture. In alternate embodiments, the second pre-selected temperature is selected such that the temperature of the second refrigerant vapor in the second condenser is at a temperature that is greater than at least the boiling point of the mixture. The process can optionally include the step of, prior to the separation steps, contacting at least a portion of the refrigerant mixture with a sorter agent such that at least a portion of one of the components of the refrigerant mixture is preferentially absorbed into the sorter agent.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DESCRIPTION OF THE INVENTION

Although the following detailed description contains many specific details for purposes of illustration, it is understood that one of ordinary skill in the art will appreciate that many examples, variations and alterations to the following details are within the scope and spirit of the invention. Accordingly, the exemplary embodiments of the invention described herein are set forth without any loss of generality to, and without imposing limitations thereon, the claimed invention.

In one aspect, the present invention provides a method for effecting the separation of individual refrigerant fluids from an azeotropic mixture thereof. In certain embodiments, the present invention provides a method for the separation and purification of individual refrigerant fluids from an azeotropic mixture thereof.

As used herein, azeotropic mixtures are defined as mixtures of two or more fluids that are present in a ratio such that the composition of the mixture cannot be changed by simple distillation of the mixture. In addition, azeotropic mixtures, at their axeotropic point, have a dew point and a boiling point with the same composition. Typically, the act of boiling an azeotropic mixture provides a vapor phase having approximately the same composition as the original azeotropic mixture that is sought to be separated.

As described herein, the present invention provides a process and an apparatus for obtaining highly pure separated azeotropic refrigerant components, thus separating chlorofluorocarbons, such as CFC-11, CFC-12, and CFC-13, and hydrochlorofluorocarbons, such as HCFC-22, HCFC-123 and HCFC-124, from fluorocarbons, including perfluorocarbons, such as FC-14 and FC-116 and HFCs such as HFC-32, HFC-125, HFC-134a and HFC-152a. It is understood that the above listing of CFCs, HCFCs, and FCs is merely exemplary, and that the azeotropic mixtures described herein can include other refrigerant fluids not explicitly described herein.

Figure 1:
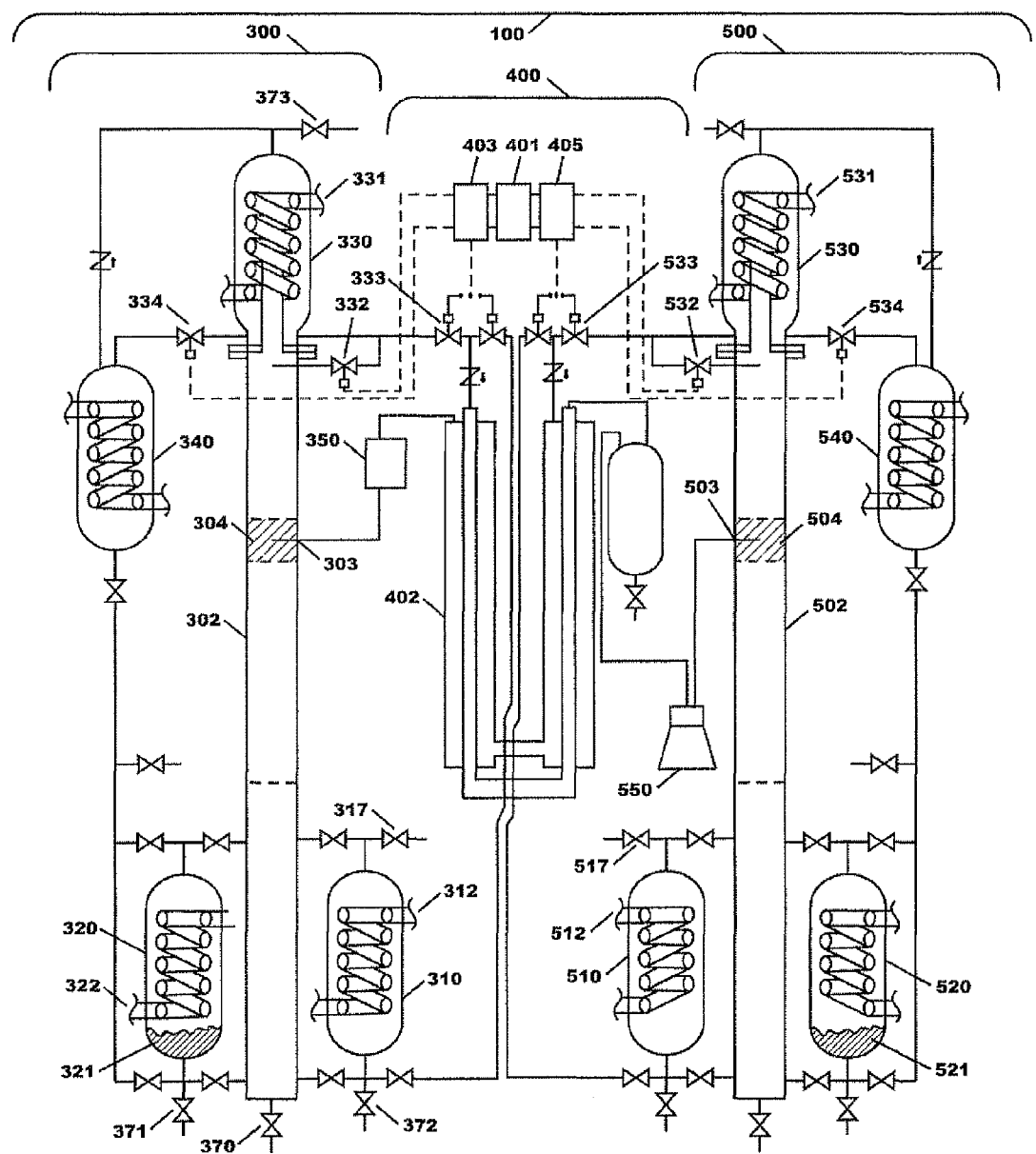
FIG. 1 is a diagram of one embodiment of an apparatus for the separation of refrigerant fluids according to the present invention.

Referring now to FIG. 1, an exemplary representation of an apparatus for the separation and purification of ideal and non-ideal fluids, according to the present invention, is provided. In one embodiment, the apparatus provides continuous means for separating and purifying the components of a mixture to a purity of 99.5% or greater.

In one embodiment of the invention, apparatus 100 is provided for the separation of refrigerant fluids. Apparatus 100 can include a first distillation unit 300 consisting of first fractionating column 302, first reboiler 310, first sorter 320, first condenser 330, first collection vessel 340, and other auxiliary equipment. Apparatus 100 can also include a second distillation unit 500 consisting of second fractionating column 502, second reboiler 510, second sorter 520, second condenser 530, second collection vessel 540, and other auxiliary equipment. Apparatus 100 can also include recirculation pump 550 and pressure regulator 350. The first unit and second unit can be fluidly connected by unit 400 through heat exchanger 402 to allow for fluids to be passed from the first distillation unit to the second distillation unit, and from the second distillation unit to the first distillation unit, as may be necessary to perform the separation and purification steps. It is understood that apparatus 100 can also include various valves for controlling the flow of refrigerant mixtures and separated product streams, as is known in the art, and that such valves can be electronically coupled to a control system (not shown).

Thus, in one embodiment, apparatus 100 can consist of two relatively simple distillation units, 300, 500, that include first and second fractionating columns, 302 and 502, respectively, which can be optionally modified to include packing. First fractionating column 302 can be fluidly connected to first reboiler 310, first sorter vessel 320, first heating means 322, and may also be connected to other auxiliary devices, such as temperature sensors, pressure gauges, and a first fractionating column bottom connection 370 for draining the first fractionating column. Apparatus 100 can also include sorter bottom connection 371 and reboiler bottom connection 372, each of which can be used for charging the system with a sorter agent or refrigerant mixture, respectively. Fractionating distillation column 302 may optionally include a sieve-plate column with a number of perforated plates or trays (not shown) stacked one above the other, or a column packed with a high efficiency packing, having, for example, a column diameter/packing size ratio ranging from about 8 to 64, or mixture thereof. The reflux condensate is returned to the top of the column 302, and secondarily can be fed to central port 503 of the middle of the second fractionating column 502. In certain embodiments, the apparatus can include various vessels for storage of refrigerant mixtures, separated refrigerants, and sorter agents, which can optionally be supplied as a make-up stream, as may be necessary from time to time.

Each fractionating column 302, 502 may be between about 1 m and about 10 m in length, and may have an inside diameter of between about 2 cm and 40 cm, although it is understood that the use of fractionating columns that are longer or shorter, or have a larger or smaller inner diameter than specified herein are within the scope of the invention. In certain embodiments, first and second fractionating columns 302, 502 can be packed with a high efficiency packing (not shown) made of stainless steel, copper, Monel (nickel alloy), steel, ceramics, or the like, wherein in certain embodiments the packing is sized from about 0.12 inch to about 0.36 inch (i.e., about 3 mm to about 9 mm). Packing that is larger than, or smaller than, that which is specified herein, is within the scope of the invention. The packing can be supplied to the fractionating column to provide a random packing that includes void spaces therein. In certain embodiments, efforts can be made, during the packing of the fractionating column, to ensure the presence of void spaces within the packing. The packing can be divided in two or more sections by redistributor zone 304, 504, wherein each packing section can have a size approximately 100 to 150 times the packing size. In certain embodiments, the redistributor zone 304, 504 can include structured packing, as is known in the art, and is available from manufacturers such as Koch-Otto York Separations Technology and Koch-Glitsch. Thus, in certain embodiments, the structured packing may include a wire mesh, for example, a stainless steel wire mesh. In one embodiment, fractionating column 302, 502 can have multiple redistributor zones 304, 504. In an exemplary embodiment, fractionating column 302, 502 can have between 4 and 8 packing sections and an equal number of redistributor zones 304, 504. In certain embodiments, redistributor zones 304, 504 may have a height of about 10 to about 15 times the packing size. In certain embodiments wherein two or more redistributor zones 304, 504 are present in respective fractionating column 302, 502, each redistribution zone may have a different height from each other redistribution zone. Alternatively, each redistribution zone 304, 504 in fractionating columns 302, 502 may have a uniform height. In certain embodiments, the height of the redistributor zone can be between about ⅕ and ⅓ the height of the packing section. Alternatively, the height of the redistributor zone can be between about ⅛ to ¼ of the height of the packing section.

In certain embodiments, first fractionating columns 302, first reboiler 310, first sorter vessel 320, first condenser 330, and first collection vessel 340 can each be constructed of stainless steel, carbon steel, or an equivalent material. Similarly, second fractionating column 502, second reboiler 510, second sorter vessel 520, second condenser 530, and second collection vessel 540, can each be constructed of stainless steel, carbon steel, or an equivalent material. In certain embodiments, recirculation pump 550 and pressure regulator 350 can be made of stainless steel, carbon steel or equivalent.

In certain embodiments, apparatus 100 is constructed of materials suitable to allow operation of the apparatus at conditions suitable for the processes described herein, such as temperatures and pressures greater than ambient conditions, preferably at pressures up to about 500 psi and temperatures of up to about 200° F.

First fractionating column 302 can also include condenser 330, cooling means 331 for the condensation of the refrigerant vapor at the top of the column, and air release valve 373. Air release valve 373 is positioned at the top of the first fractionating condenser 302 to prevent inert accumulation in the condenser. First fractionating column 302 can also include a variable reflux control for solenoid valve 332 that controls the return of condensate to the column, and solenoid valve 333 for controlling drainage from condenser 330 to the concentric heat exchanger 402. During typical operation of the fractionating column under reflux conditions, valve 332 is typically maintained in the open position and valve 333 is maintained in the closed position. In certain embodiments, second fractionating column 502 can be configured virtually identically to first fractionating column 302. Second fractionating column 502 similarly includes second condenser 530, cooling means 531, and an air release valve. Solenoid controls 532 and 533 can be used to control the flow of the condensate to the heat exchanger 402.

Central feed port 303 of first fractionating column 302 and the central feed port 503 of second fractionating column 502 are inlet points for the azeotropic mixtures. The azeotropic mixture can be supplied from condenser 330, via solenoid valve 333, to central feed port 503 of second fractionating column 502 by recirculation pump 550. Similarly, the azeotropic mixture from second condenser 530, coupled to second fractionating column 502, is supplied via solenoid valve 533 to central feed port 303 of first fractionating column 302 and is controlled by pressure regulator 350. The azeotropic mixtures from the first and second distillation units 300, 500 flow in a counter current fashion through concentric pipe heat exchanger 402 when the mixture, controlled by solenoid valve 333 and solenoid valve 533, is supplied.

Purity of the refrigerant or refrigerant mixture can be sampled at various positions in the device. For example, reboilers 310 and 510 are fluidly connected to valves 317 and 517 respectively, which thereby allows for sampling of the flow, at the specific positions within the apparatus. Sampling can be automated, or can be done manually.

In certain embodiments, it is possible to include additional distillation units having similar components to those have been described herein with respect to distillation units 300 and 500. In these embodiments having greater than two distillation units, additional units are connected in series. Each distillation unit is connected to an adjacent distillation unit by a control unit, wherein the additional control units have similar components to control unit 400.

In addition to the components described herein, in certain embodiments, the apparatus for separating and purifying refrigerant mixtures can include a computing device (not shown) selected from one or more networked personal computer, laptop, server, or the like. The computing device can include instructions for the operation of apparatus 100. The computing device can include computer instruction code, such as for example, Java, C, C++, Visual Basic, and the like. The software code can be stored as a series of instructions or commands on a readable computer medium, including random access memory, read only memory, a magnetic medium, such as for example, a hard drive or floppy disc, an optical medium, or like device. In addition, the computing device can include software operable to provide results related to absolute particle counts, mean particle size, mass distribution, percentage distribution, total suspended solids, and standard deviation.

The computer can be configured to send and receive signals to various components of the apparatus. For example, in certain embodiments, the computer can be configured to send signals to the various valves within the apparatus to control the flow of fluids therein. Alternatively, the computer can be configured to send signals to the various temperature controllers that are operatively coupled to the condensers, reboilers, sorters and collection vessels to provide instructions for providing heating or cooling, as needed.

Additionally, the apparatus can include a computer program product, associated first and second distillation units, and the equipment associated therewith, and stored on a tangible computer memory media and operable on the computer. The computer program product includes a set of instructions which, when executed by the computer, cause the computer to perform various operations related to controlling and providing instructions to the various components and peripheral devices connected to the separation apparatus.

In one embodiment, the process and the apparatus described herein are particularly useful with respect to the separation and purification of non-ideal binary homogeneous azeotropic mixtures. In certain embodiments, the process and apparatus described herein is particularly useful in treating mixtures having a minimum azeotrope boiling point, such as the CFC-12/HFC-134a azeotrope, and can include the use of sorter agents, for example a hydrocarbon and glycol, such as n-decane, and diethylene glycol, respectively, in each sorter vessel.

The steps of the treatment of a non-ideal azeotropic mixture can include introducing the mixture into first reboiler vessel 310 of first fractionating column 302 and into second reboiler 510 of second fractionating column 502. First reboiler vessel 310 can be used to load the inventory of the refrigerant mixture to first fractionating column 302 and can be heated by first heating means 312. Second reboiler vessel 510 can similarly be used to load the inventory of the refrigerant mixture to second fractionating column 502 and can be heated by second heating means 512. As heating of first and second reboilers 310, 510 begins, the azeotropic mixture vaporizes and the refrigerant vapor travels up within first fractionating column 302 to condenser 330, where the vapor is condensed with cooling means 331 to form a liquefied azeotropic mixture by the use of cooling means 331. Similarly, the process can operate in condenser 530, wherein vapor is condensed by cooling means 531. Cooling means 331 is typically a coil or cold finger that is maintained at a temperature below the boiling point of the azeotropic mixture. The condensate can be partially drained via solenoid valve 332, and returned to first fractionating column 302. A portion of the condensate can also be diverted to the heat exchanger 402 and second fractionary column 502 by opening solenoid valve 333.

In the exemplary azeotropic binary mixture that includes CFC-12 and HFC-134a, the CFC-12 component of the azeotropic binary mixture can optionally be absorbed by an absorbent sorter agent, such as n-decane. In desorption mode, the CFC-12 component absorbed in the hydrocarbon (e.g., n-decane) can be desorbed from the sorter agent by turning on second heating means 512, and separating the hydrocarbon and refrigerant by distillation. In certain embodiments, the sorter agents have lower vapor pressures than the refrigerant that is desired to be separated, thereby allowing relatively simple separation of the refrigerant from the sorter agent by distillation. The reflux control for second fractionating column 502 can be maintained at a full reflux by keeping solenoid valve 532 open and solenoid valve 533 closed. The reflux control for first fractionating column 302 can be maintained at a full reflux by keeping solenoid valve 333 closed and solenoid valve 332 open. Recirculation pump 550 can be turned on to pull the azeotropic mixture of CFC-12/HFC-134a refrigerants from condenser 330 through heat exchanger 402 and into Second fractionating column 502 through central port 503.

In certain embodiments, a refrigerant can be used as the sorter. For example, in certain embodiments, HFC-134a can be used as a sorter for a mixture of CFC-12 and HCFC-22. Additionally, in certain embodiments, HCFC-22 can be used as a sorter for separating a mixture of HFC-32 and HFC-125.

The quality of the CFC-12 refrigerant separated from the azeotropic mixture can be checked at sample analyzer 517. This quality check is used to determine if the concentration of the CFC-12 component of the mixture is greater than it was in the original azeotropic mixture. Once the desired purity of the CFC-12 component is achieved, the solenoid valve 334 can then be opened to the collection vessel 340. The HFC-134a product collected in collection vessel 340 is purified to a purity of 99.5% or greater. The HFC-134a component is collected in reboiler vessel 310 at a complementary purity of 99.5% or greater. The CFC-12 component is collected in sorter vessel 520, along with the sorter agent N-decane, at a purity of 99.5%.

In certain embodiments, first fractionating column 302 can operate as a simple stand alone distillation column when solenoid valve 334 is connected to control timer 401 via switch 403. First fractionating column 302 can also operate as an azeotropic distillation column when solenoid valve 333 is connected to control timer 401 via switch 403. Similarly, second fractionating column 502 can operate as a simple distillation column when solenoid valve 534 is connected to control timer 401 via switch 405. Second fractionating column 502 can also operate as an azeotropic distillation column when solenoid valve 533 is connected to timer 401 via switch 405.

In certain embodiments, the process for the separation of a binary azeotropic mixture proceeds in a two step process, wherein during the first step, the binary mixture is contacted with a sorter agent, which can preferentially absorb one component from the binary azeotrope mixture over another component within the mixture. The process then proceeds as a simple distillation process. The first step azeotropic mode separates the two components, such that there is but a single component in each column. The second step distillation can then extract the refrigerant component from the sorter agent, thereby providing a purified refrigerant.

Among the refrigerant fluids that make up the various azeotropic mixtures, a number of the refrigerant fluids have boiling points that are particularly close to each other. For example, chlorofluorocarbon CFC-12 (boiling point −29.3° C.) and fluorocarbon HFC-134a (boiling point −26.2° C.) have boiling points that are within 3° C. of each other. With such mixtures, it may be desirable to incorporate sorter agents during the process, utilizing a sorter agent that is preferential for one of the components. The sorter agent can be selected based upon a number of criteria, such as based upon the affinity of the sorter agent to absorb a given refrigerant compound. Additionally, the sorter agent can be selected such that the agent has a much lower vapor pressure than the refrigerant for which it is used. Typically, a sorter agent is selected that is preferential toward the chlorofluorocarbon component of the mixture, e.g. R-12. Exemplary sorter agents that are preferential toward the chlorofluorocarbon component include hydrocarbons that have between about 6 and 20 carbon atoms and mixtures thereof. It is understood that, in certain embodiments, hydrocarbons have fewer than 6 carbon atoms or more than 21 carbon atoms may be used as sorter agents. One exemplary hydrocarbon used as a sorter vessel in the present invention is n-decane, which has a melting point of −90.6° C. and a boiling point of 98.4° C. Other compounds that can be used as sorter agents include aliphatic monohydric alcohols having between 1 and 10 carbon atoms, or polyols having between 2 and 10 carbon atoms, and mixtures thereof. An exemplary monohydric alcohol is ethanol, having a boiling point of 78.4° C., and an exemplary polyol is ethylene glycol, having a boiling point of 197.9° C. The process of the present invention has great flexibility of temperature operation (i.e., the temperature of the liquid in the reboiler), for instance from about, but not limited to, −40° C. to about 100° C.; the process temperature of the refrigerant.

In one embodiment, the apparatus can be utilized for the distillation of an ideal binary mixture. As used herein, ideal binary mixture refers to a mixture of components that do not form an azeotrope. Separation of the ideal binary mixture only requires first fractionating column 302, wherein the separation is achieved by simple distillation, wherein the low boiling component can be purified and collected in collection vessel 340 and the high boiling component is purified and collected in reboiler 310. Examples of simple distillation include an HCFC-22/HFC-134a mixture or an HCFC-22/HFC-32 mixture. Apparatus 100, having two distillation units 300, 500, can thus operate each distillation separately from the other, thereby allowing the separation of two refrigerant mixtures to proceed simultaneously.

In an alternate embodiment, the apparatus can be used to process and separate a non-ideal azeotropic mixture. If the mixture is a non-ideal binary mixture, having a minimum azeotropic boiling point, the concentration of the two components at the minimum azeotropic boiling point changes with the equilibrium temperature. Exemplary mixtures include CFC-12/HFC-134a and CFC-12/FC-152a mixtures. This type of non-ideal azeotropic binary separation requires the use of both the first and second fractionating columns 302, 502 where, by recirculation of the azeotrope through the two fractionating columns, and control of the temperature differential between the operating temperature of the condenser 330 and the operating temperature of the condenser 530. When the composition of the two components of the azeotropic binary mixture at the azeotropic boiling point changes with any change of the equilibrium temperature, the volatility of the pure components decreases with a the use of a sorter agent and for each pure component the separation of the components is accelerated. For the separation of an exemplary azeotropic mixture that includes CFC-12 and HFC-134a, the CFC-12 component is collected in the reboiler 510 and HFC-134a component is collected in the reboiler 310. In embodiments wherein the composition of the two components of the azeotropic binary mixture at the azeotropic boiling point is unaffected with any change of azeotropic equilibrium temperature; a sorter agent is required for at least one refrigerant component for the separation of the components. An exemplary azeotropic mixture likely to require a sorter agent is an HCFC-22/HFC-125 mixture. In general refrigeration mixtures of CFCs, HCFCs, HFCs and FCs are ideal or non-ideal mixtures.

Apparatus 100 can be run as a batch process, a continuous batch process, or continuously. In certain embodiments wherein the process is run continuously, the feed rate of additional refrigerant mixture can be equal to the rate of production of the purified refrigerant.

EXAMPLES

The following examples are used as an illustration of embodiments of the present invention.

Example 1

Figure 2:
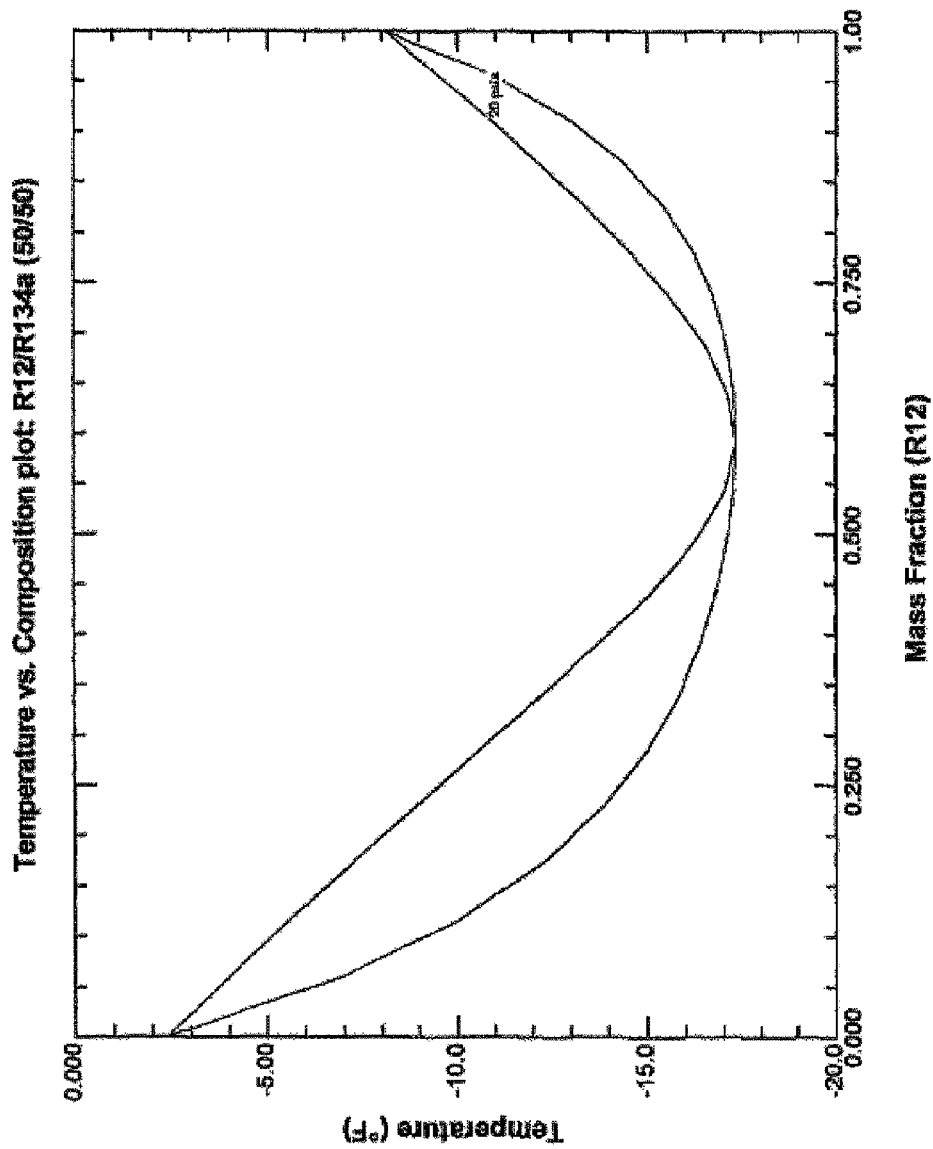
FIG. 2 is a temperature vs. composition plot for a mixture comprising 50% by weight R12 and 50% by weight R134a at a pressure of 20 psia.
Figure 3:
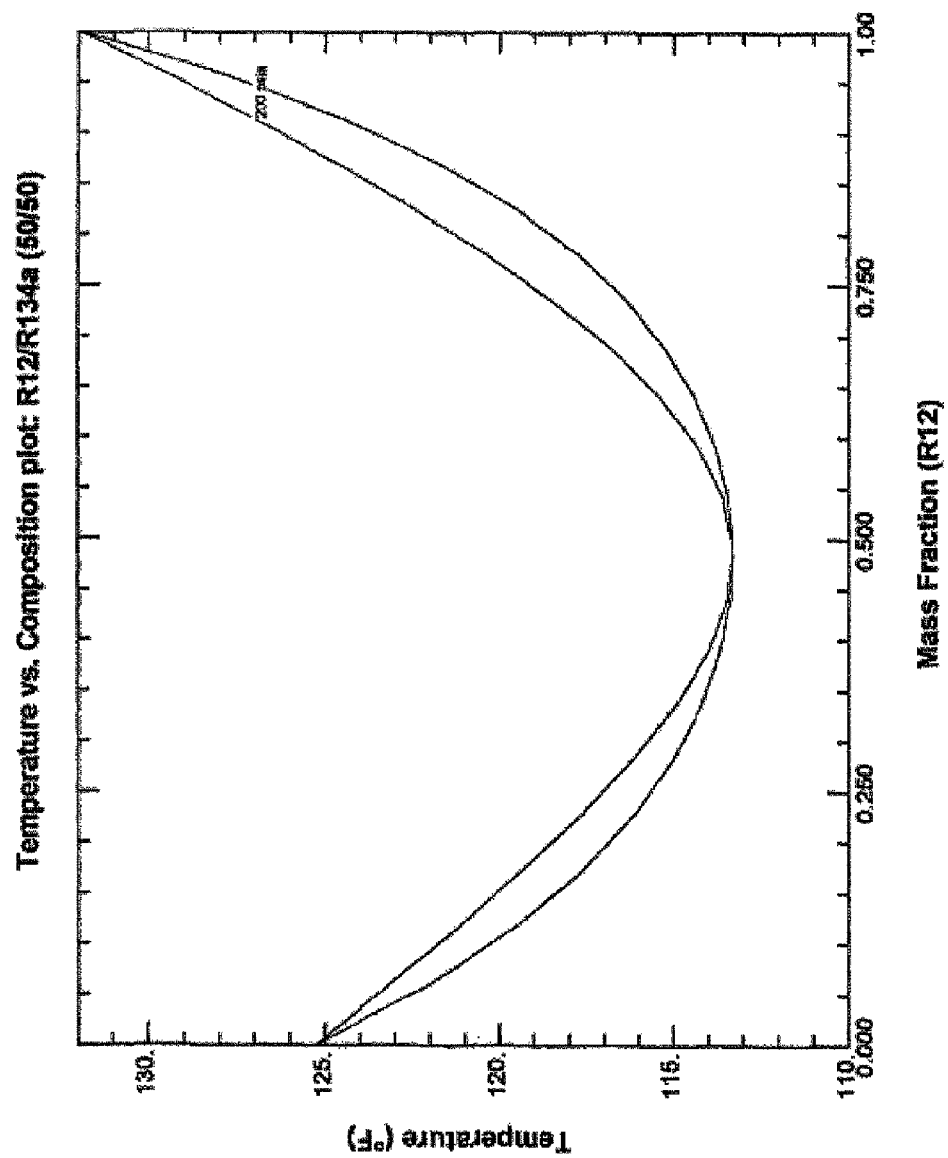
FIG. 3 is a temperature vs. composition plot for a mixture comprising 50% by weight R12 and 50% by weight R134a at a pressure of 200 psia.

Referring to FIG. 1, sorter vessel 320 was charged with 300 lbs of ethylene glycol sorter agent and 300 lbs of an azeotropic binary mixture that includes CFC-12 and HFC-134a (as shown in FIG. 2, wherein the equilibrium of temperature vs. composition at a constant saturation pressure is provided). Sorter vessel 520 was charged with 300 lbs of mineral oil sorter agent 521 and 300 lbs of the azeotropic binary of CFC-12 and HFC-134a (as shown in FIG. 3, wherein the equilibrium of temperature vs. composition at a constant saturation pressure is provided). Condenser 330 and reboiler 310 were operated at a temperature range of between about −20° F. and 0° F. and condenser 530 and reboiler 510 were operated at a temperature range of between about 110° F. and 135° F. Reflux control timer 401 was set at a reflux ratio of between 1/1 to 30/1, and distillate from condenser 330 flowed, via solenoid valve 333, through heat exchanger 402 by use of recirculation pump 550, and was fed to second fractionating column 502. Simultaneously, distillate from condenser 530 flowed, via solenoid valve 533, through heat exchanger 402 by means of pressure regulator 350, and was fed via central feed port 303 to fractionating column 302. After about 10 hrs of steady state operation and maintaining a reflux of the azeotropic mode, a liquid product accumulated in the reboilers coupled to each of the first and second fractionating columns having a purity of greater than about 99.5%. The individual component in each reboiler were then extracted.

Example 2

The same apparatus utilized in Example 1 was utilized. Reboilers 310 and 510 were each charged with about 360 lbs of dry R-500 with the sorter agents of Example 1 remaining in the system. Condenser 330 and reboiler 310 were operated at a temperature range of between about 40° F. and −40° F. and condenser 530 and reboiler 510 were operated at a temperature range of between about 60° F. to 160° F. The azeotrope mixture was recirculated from condenser 330 to the central feed port 503 of fractionating column 502, and recirculation of the azeotropic mixture is recirculated from condenser 530 to the central feed port 303 of fractionating column 302. After approximately 12 hrs of steady state operation, a CFC-12 product was collected in reboiler 510 and an HFC-152 product was collected in reboiler 310, wherein each product had a purity of 99.5%.

Example 3

Figure 4:
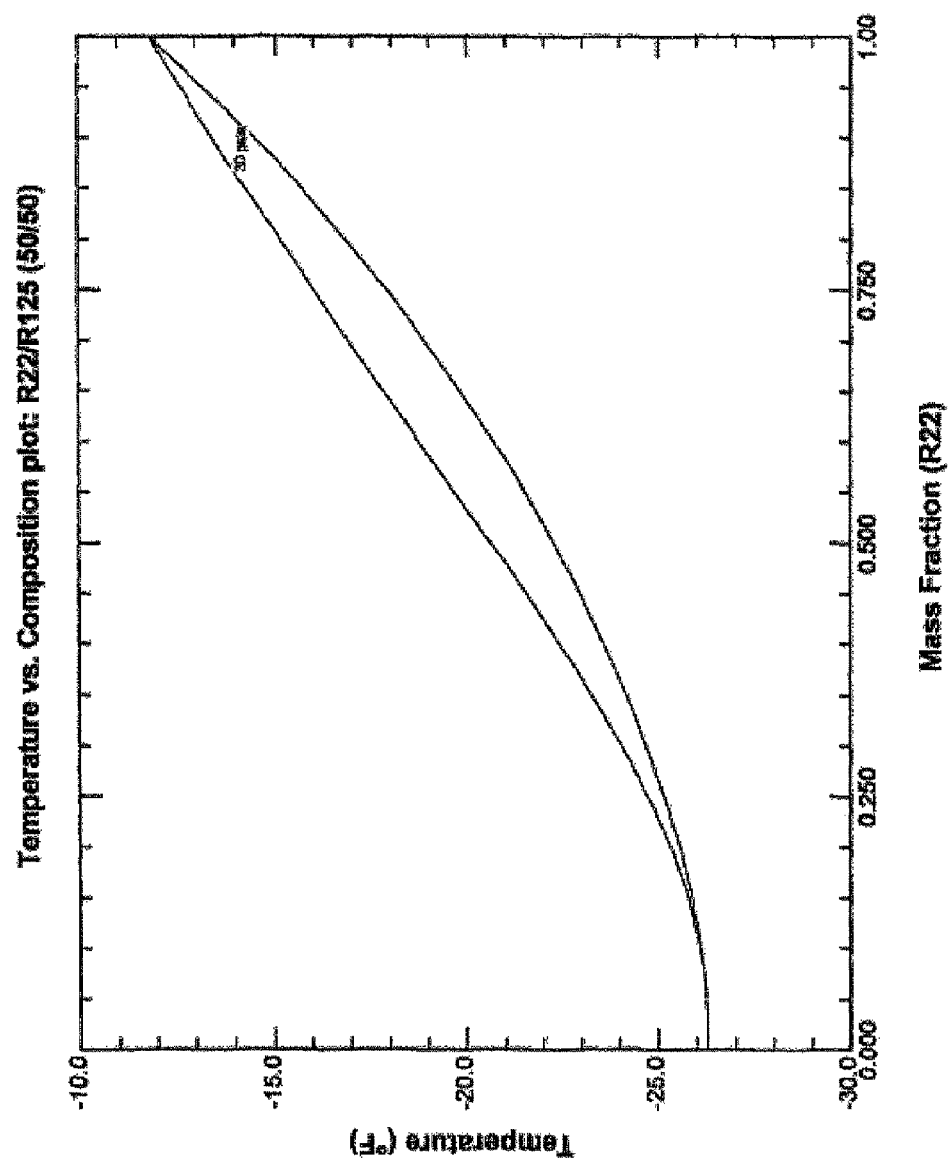
FIG. 4 is a temperature vs. composition plot for a mixture comprising 50% by weight R22 and 50% by weight R125.

Reboiler 310 was charged with approximately 1000 lbs of a binary mixture that includes about 85% of HCFC-22 and about 15% of HFC-125. During distillation, the azeotropic composition was about 80% HFC-125 and 20% HCFC-22 (as shown in FIG. 4, wherein the equilibrium of temperature vs. composition at a constant saturation pressure is provided). Condenser 330 and reboiler 310 were operated at a temperature of between about −10° F. and −30° F. At the end of the process, about 800 lbs of HCFC-22 having a purity of about 99.5% was collected from reboiler 310 and about 200 lbs of the azeotropic mixture was collected in the collection vessel 340. The sorter vessel 320 was charged with about 100 lbs of sorter agent and the azeotropic mixture from the collection vessel 340 was supplied to the bottom of sorter vessel 320, and allowed to bubble up through the butyl carbitol sorter agent. Reboiler 310 was isolated and distillation of the azeotropic mixture was initiated by using the sorter vessel 320 as a reboiler. After the equilibrium was established, about 140 lbs of the HFC-125 was collected in the collection vessel 340 having a purity of about 99.5%.

Example 4

Figure 5:
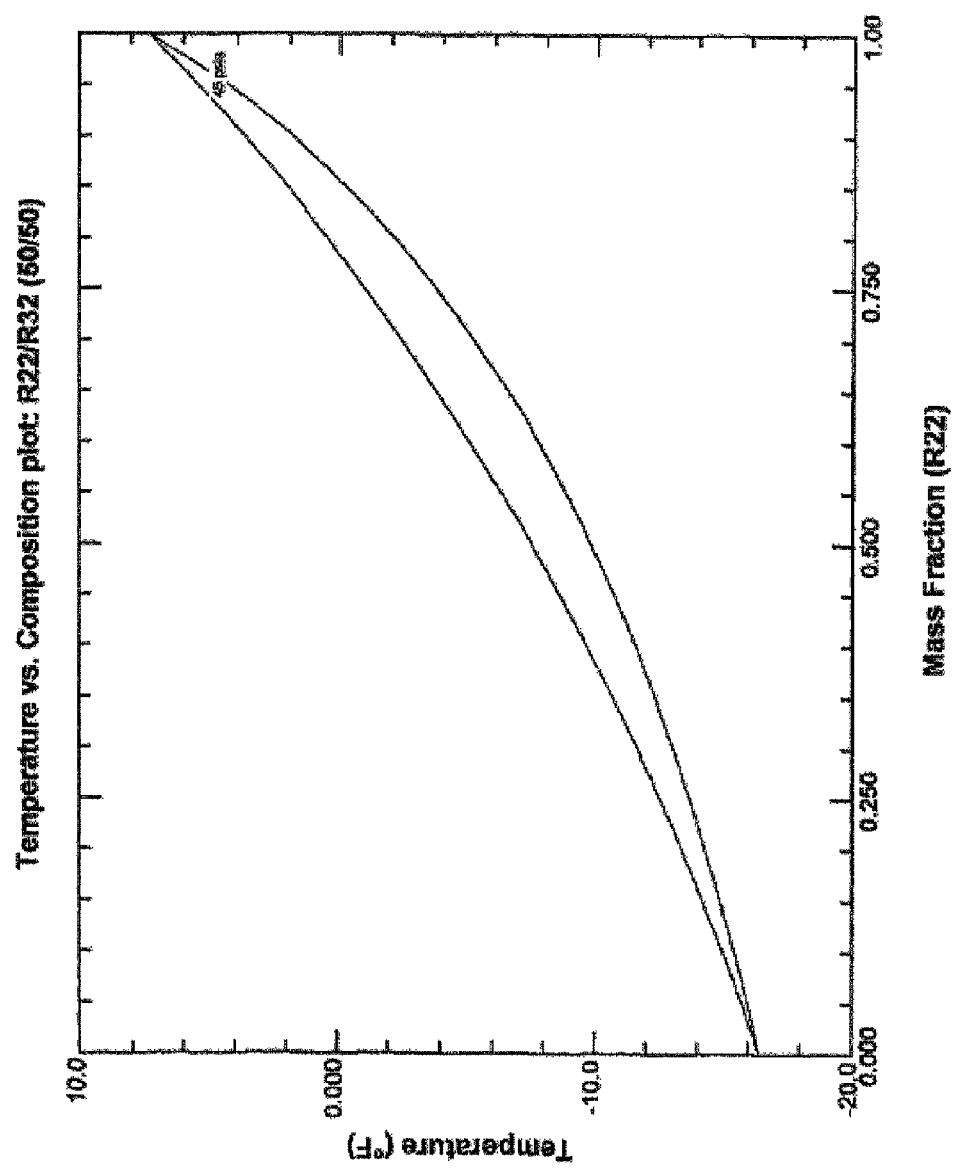
FIG. 5 is a temperature vs. composition plot for a mixture comprising 50% by weight R22 and 50% by weight R32.

Reboiler 310 was charged with about 1000 lbs of an ideal binary mixture that included about 85% HCFC-22 and 15% of HFC-32 (as shown in FIG. 5, wherein the equilibrium of temperature vs. composition at a constant saturation pressure is provided). Condenser 330 and reboiler 310 were operated at a temperature range of between about −20° F. to 10° F. A simple distillation took place after the equilibrium is established. The reflux ratio was set at 20/1, and about 150 lbs of HFC-32, at a purity of 99.5%, was collected in the collection vessel 340 and the about 850 lbs of HCFC-22, at a purity of 99.5%, was collected in the reboiler 310. The fractionating column 302 was arranged as a simple distillation column for an ideal mixture.

Example 5

Figure 6:
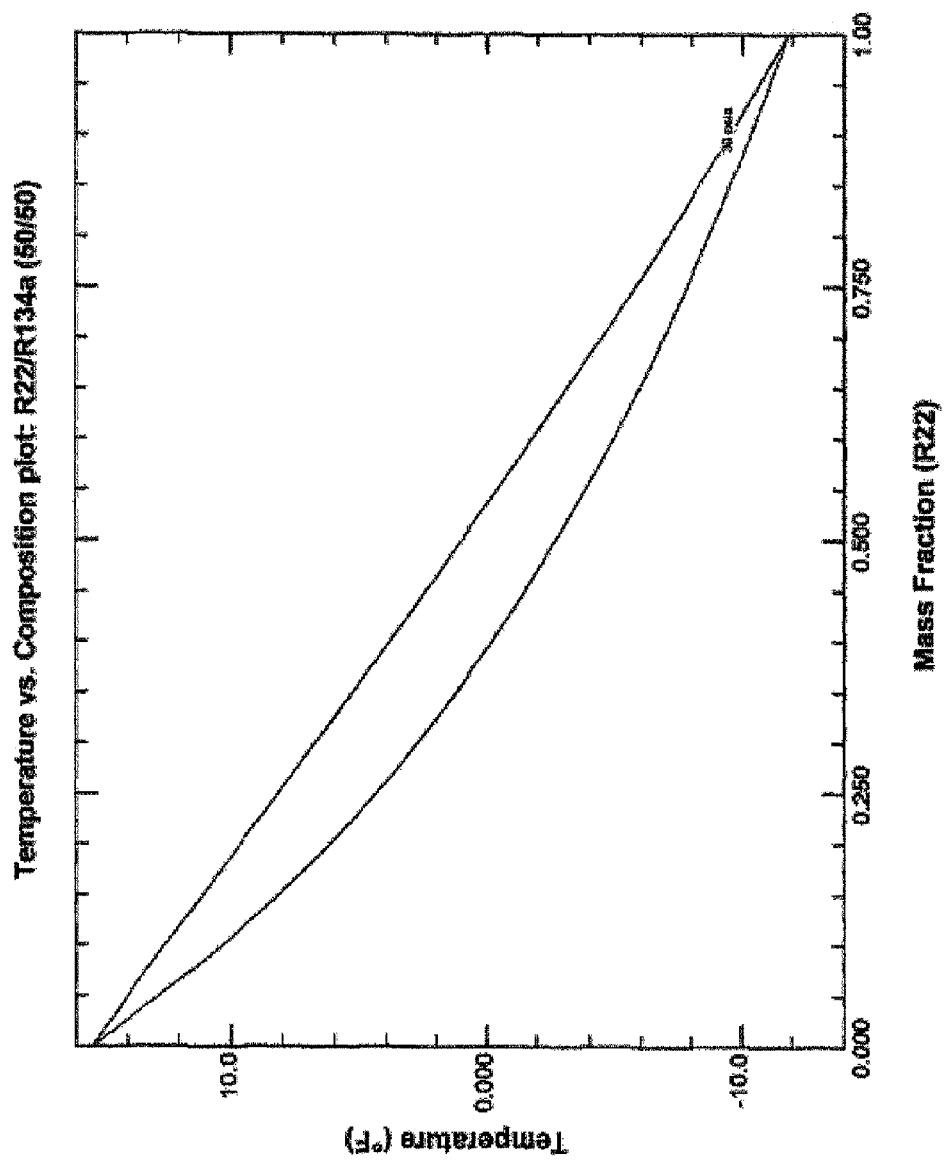
FIG. 6 is a temperature vs. composition plot for a mixture comprising 50% by weight R12 and 50% by weight R134a at a pressure of 30 psia.

Reboiler 310 was charged with about 1000 lbs of a 50/50 mixture of HCFC-22 and HFC-134a (as shown in FIG. 6, wherein the equilibrium of temperature vs. composition at a constant saturation pressure is provided). Condenser 330 and reboiler 310 were operated at a temperature range of between about −14° F. to 16° F. According with the equilibrium temperature vs. composition, a simple distillation of an ideal binary mixture was used for the separation of the two components at a temperature range of between about −14° F. to 16° F. at a constant pressure of 30 psia. The HCFC-22 was purified to 99.5% in the condenser 330 and collected in the collection vessel 340. The HFC-134a was purified to 99.5% and collected in the reboiler 310. The operation conditions were the same as were described as in example 4.

It will be apparent to those skilled in the art that modifications in the apparatus may be made within the scope of the claims as well as adjustments for processing of various azeotropic mixtures.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

The singular forms "a", "an" and "the" include plural referents, unless the context clearly dictates otherwise.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

Throughout this application, where patents or publications are referenced, the disclosures of these references in their entireties are intended to be incorporated by reference into this application, in order to more fully describe the state of the art to which the invention pertains, except when these reference contradict the statements made herein.

That which is claimed is:

1. A process for separating a refrigerant mixture comprising a first and second refrigerant component comprising the steps of:
   introducing the refrigerant mixture into a first and second sorters and contacting the refrigerant mixture with a sorter agent, wherein the step of contacting the refrigerant mixture with the sorter agent preferentially absorbs the first refrigerant component from the refrigerant mixture;
   heating the first sorter to a first pre-selected temperature to produce a second refrigerant vapor;
   cooling the second refrigerant vapor using a first distillation column and producing a second refrigerant component condensate in a first condenser, the second refrigerant component condensate being essentially free of the first refrigerant component;
   transferring the condensate from the first condenser to a second distillation column;
   collecting a first product stream from the first distillation column, wherein the first product stream comprises the second refrigerant component;
   heating the second sorter to a second preselected temperature to produce a first refrigerant vapor;
   cooling the first refrigerant vapor using the second distillation column and producing a first refrigerant component condensate in a second condenser, the first refrigerant component condensate being essentially free of the second refrigerant component;
   transferring the condensate from the second condenser to the first distillation column; and
   collecting a second product stream from the second distillation column, wherein the second product stream comprises the first refrigerant component,
   wherein the transferring steps of the condensates from the first and second condensers to the second and first distillation columns respectively is accomplished using a heat exchanger that is fluidly connected to the first and second condensers and to the first and second distillation columns.

2. The process of claim 1 wherein the refrigerant components in the refrigerant mixture are selected from the group consisting of chlorofluorocarbons, hydrochlorofluorocarbons, hydrofluorocarbons and fluorocarbons.

3. A process for separating a refrigerant mixture comprising two refrigerant components, the process comprising the steps of:
   introducing equal volumes of the refrigerant mixture into a first and second reboilers of an apparatus comprising a first and second distillation columns and a heat exchanger fluidly connected to the first and second distillation columns such that the heat exchanger is positioned to received condensate from a first condenser and a second condenser and to transfer the condensate from the first condenser to the second distillation column, and to transfer the condensate from the second condenser to the first distillation column;
   heating the refrigerant mixture in the first reboiler to a first pre-selected temperature such that the first reboiler produces a first refrigerant vapor;
   heating the refrigerant mixture in the second reboiler to a second pre-selected temperature such that the second reboiler produces a second refrigerant vapor;
   cooling the first refrigerant vapor in the first condenser to form a first refrigerant condensate;
   cooling the second refrigerant vapor in the second condenser to form a second refrigerant condensate;
   collecting a portion of the first refrigerant condensate from the first condenser and transferring it to the second distillation column, wherein the first refrigerant condensate has a greater concentration of one component of the refrigerant mixture than the first refrigerant vapor;
   collecting a portion of the second refrigerant condensate from the second condenser and transferring it to the first distillation column, wherein the second refrigerant condensate has a greater concentration of one component of the refrigerant mixture than the second refrigerant vapor;
   repeating the separation steps until the first and second refrigerant condensates reach a pre-selected purity; and then
   collecting a first product stream comprising a portion of the first refrigerant condensate in a first collection vessel; and collecting a second product stream comprising a portion of the second refrigerant condensate in a second collection vessel.

4. The process of claim 3, wherein the first pre-selected temperature is selected such that the temperature of the first refrigerant vapor in the first condenser is at a temperature that is greater than at least the boiling point of the refrigerant mixture.

5. The process of claim 3 wherein the refrigerant components in the refrigerant mixture are selected from the group consisting of chlorofluorocarbons, hydrochlorofluorocarbons, hydrofluorocarbons and fluorocarbons.

6. The process of claim 3 wherein the second pre-selected temperature is selected such that the temperature of the second refrigerant vapor in the second condenser is at a temperature that is greater than at least the boiling point of the mixture.

7. The process of claim 3 wherein the pressure in the first distillation column is kept constant during the separation of the refrigerant mixture.

8. The process of claim 3 wherein the pressure in the second distillation column is kept constant during the separation of the refrigerant mixture.

9. The process of claim 3, further comprising:
   prior to the separation steps, contacting at least a portion of the refrigerant mixture with a sorter agent such that at least a portion of one of the components of the refrigerant mixture is preferentially absorbed into the sorter agent.

10. The process of claim 3 further comprising testing the purity of at least one of the first and second refrigerant condensates.

11. The process of claim 3, wherein the first product stream has a purity of at least 99.5%.

12. The process of claim 3, wherein the second product stream has a purity of at least 99.5%.

* * * * *